United States Patent
Pham et al.

(10) Patent No.: US 6,534,467 B2
(45) Date of Patent: Mar. 18, 2003

(54) AZEOTROPE-LIKE COMPOSITION OF 1,2,2-TRICHLORO-1,3,3,3-TETRAFLUOROPROPANE AND HYDROGEN FLUORIDE

(75) Inventors: Hang Thanh Pham, Erie County, NY (US); Rajiv Ratna Singh, Erie County, NY (US); Hsueh Sung Tung, Erie County, NY (US)

(73) Assignee: Honeywell International Inc., Morristown, NJ (US)

( * ) Notice: Subject to any disclaimer, the term of this patent is extended or adjusted under 35 U.S.C. 154(b) by 44 days.

(21) Appl. No.: 09/768,638

(22) Filed: Jan. 24, 2001

(65) Prior Publication Data

US 2002/0137646 A1 Sep. 26, 2002

(51) Int. Cl.$^7$ ................................................. C11D 7/50
(52) U.S. Cl. ........................ 510/408; 510/405; 510/407; 510/175; 510/176; 510/177
(58) Field of Search ..................... 510/405, 407, 510/408, 175, 176, 177

(56) References Cited

U.S. PATENT DOCUMENTS

| | | | |
|---|---|---|---|
| 5,496,866 A | | 3/1996 | Sommerfeld et al. |
| 5,574,192 A | | 11/1996 | Van Der Puy et al. |
| 6,329,559 B1 | * | 11/2001 | Sivert et al. |

FOREIGN PATENT DOCUMENTS

| | | |
|---|---|---|
| WO | WO 91 01287 A | 2/1991 |
| WO | WO 99 62849 A | 12/1999 |

* cited by examiner

*Primary Examiner*—Gregory E. Webb
(74) *Attorney, Agent, or Firm*—Synnestvedt & Lechner LLP

(57) ABSTRACT

The invention relates to azeotropic and azeotrope-like mixtures of 1,2,2-trichloro-1,3,3,3-tetrafluoropropane (commonly known as HCFC-224aa, and with the IUPAC name of 2,2,3-trichloro-1,1,1,3-tetrafluoropropane;registry number 139754-75-9) and hydrogen fluoride (hydrofluoric acid), which are useful as intermediates in the production of 1,1,3,3,3-pentafluoropropane (HFC-245-fa) and 1,1,1,2,2,3,3-heptafluoropropane (HFC-227ca).

7 Claims, 1 Drawing Sheet

VLLE of 224/HF

US 6,534,467 B2

AZEOTROPE-LIKE COMPOSITION OF 1,2,2-TRICHLORO-1,3,3,3-TETRAFLUOROPROPANE AND HYDROGEN FLUORIDE

FIELD OF THE INVENTION

The present invention pertains to azeotropic and azeotrope-like compositions of 1,2,2-trichloro-1,3,3,3-tetrafluoropropane (HCFC-224aa) and hydrogen fluoride.

BACKGROUND

In recent years there has been universal concern that completely halogenated chlorofluorocarbons (CFC's) might be detrimental to the Earth's ozone layer. Consequently, there is a worldwide effort to use fluorine-substituted hydrocarbons that contain fewer or no chlorine substituents. In this regard, 1,1,3,3,3-pentafluoropropane, a hydrofluorocarbon (HFC) having zero ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are also non-flammable, and non-toxic as compared to the chlorine containing compounds.

1,1,3,3,3-Pentafluoropropane (HFC-245fa) is well known in the art as described in U.S. Pat. Nos. 5,496,866 and 5,574,192, both of which are incorporated by reference herein in their entirety.

It has now been found that an intermediate in the production of substantially pure 1,1,3,3,3-pentafluoropropane, is an azeotropic or azeotrope-like mixture of 1,2,2-trichloro-1,3,3,3-tetrafluoropropane (HCFC-224aa) and hydrogen fluoride. This intermediate, once formed, may thereafter be separated into its component parts by extraction techniques. The azeotropic and azeotrope-like compositions find use as non-aqueous etching agents for etching semiconductors in the electronics industry, compositions for removing surface oxidation from metals, as well as intermediates in processes to produce further fluorinated derivatives such as 1,1,1,2,2,3,3-heptafluoropropane (HFC-227ca).

SUMMARY OF THE INVENTION

In one embodiment, the invention provides an azeotropic composition consisting essentially of 1,2,2-trichloro-1,3,3,3-tetrafluoropropane and hydrogen fluoride.

The invention further provides an azeotropic or azeotrope-like composition consisting essentially of from about 1 to about 95 weight percent hydrogen fluoride and from about 5 to about 99 weight percent 1,2,2-trichloro-1,3,3,3-tetrafluoropropane, which composition has a boiling point of from about 28° C. to about 65° C. at a pressure of from about 21 psia to about 66 psia.

In another embodiment, the invention provides a method of forming an azeotropic or azeotrope-like composition, which method comprises blending from about 1 to about 95 weight percent hydrogen fluoride and from about 5 to about 99 weight percent of 1,2,2-trichloro-1,3,3,3-tetrafluoropropane, which composition has a boiling point of from about 28° C. to about 65° C. at a pressure of from about 21 psia to about 66 psia.

In still another embodiment, the invention provides a process for removing 1,2,2-trichloro-1,3,3,3-tetrafluoropropane from a mixture of 1,2,2-trichloro-1,3,3,3-tetrafluoropropane and at least one impurity, which process comprises adding hydrogen fluoride to the mixture in an amount sufficient to form an azeotropic or azeotrope-like composition of 1,2,2-trichloro-1,3,3,3-tetrafluoropropane and hydrogen fluoride, and thereafter separating the azeotropic composition from the impurity.

DETAILED DESCRIPTION OF THE PREFERRED EMBODIMENT

Figure 1:
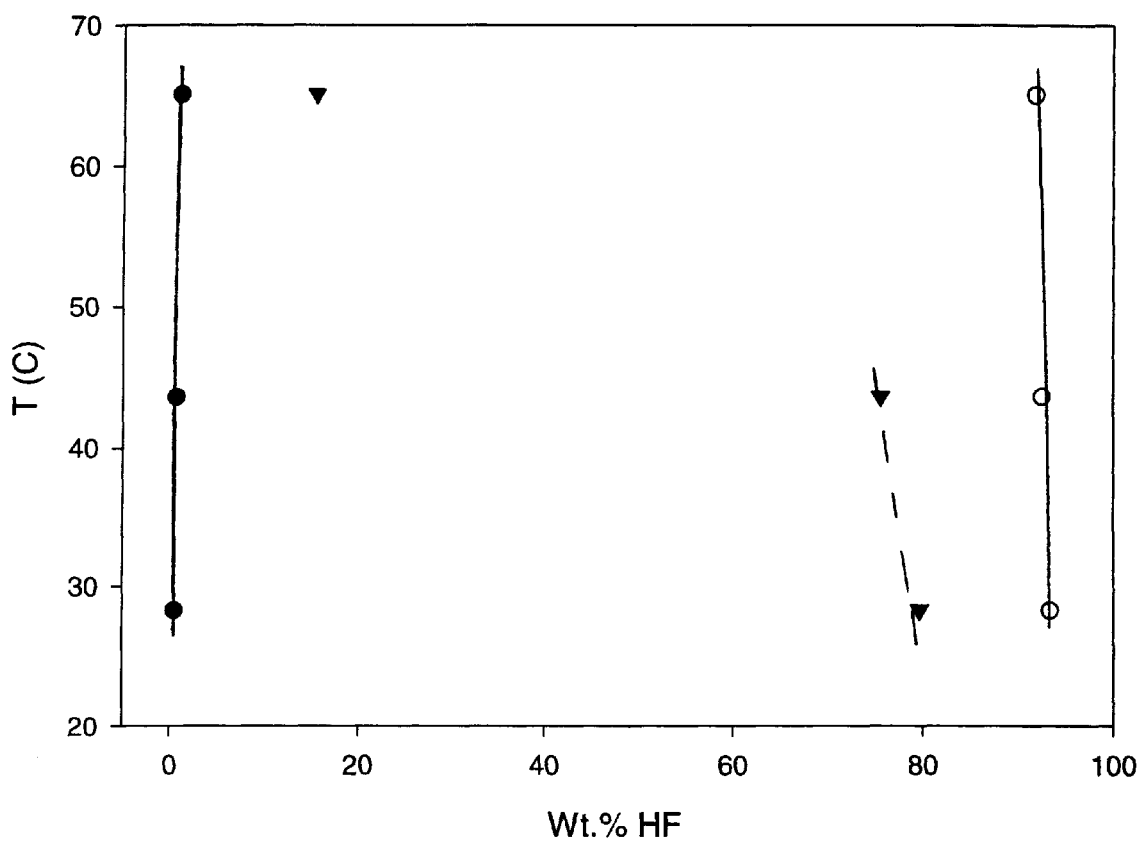
FIG. 1 shows a Vapor-Liquid-Liquid Equilibrium (VLLE) plot for HCFC-224aa and HF.
Figure 1:
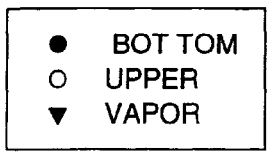

In a method of preparing HCFC-224aa, precursor reagents are fluorinated with hydrogen fluoride. The reaction products of such precursors include HCFC-224aa, unreacted HF and other by-products. Upon removal of the by-products, a binary azeotrope or azeotrope-like composition of HCFC-224aa and HF is formed. This binary azeotrope or azeotrope-like composition is then available for separation into its component parts.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation. One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance. Another characteristic of azeotrope-like compositions is that there is a range of compositions containing the same components in varying proportions that are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition comprising effective amounts of hydrogen fluoride and HCFC-224aa to form an azeotropic or azeotrope-like composition. By effective amount is meant an amount of each component which, when combined with the other component, results in the formation of an azeotrope or azeotrope-like mixture. The inventive compositions preferably are binary azeotropes that consist essentially of combinations of only hydrogen fluoride with HCFC-224aa.

In the preferred embodiment, the inventive composition contains from about 1 to about 95 weight percent HF, preferably from about 15 to about 80 weight percent and most preferably from about 70 to about 80 weight percent. In the preferred embodiment, the inventive composition contains from about 5 to about 99 weight percent HCFC-224aa, preferably from about 20 to about 85 weight percent and most preferably from about 20 to about 30 weight percent. The composition of the present invention has a boiling point of from about 28° C. to about 65° C. at a pressure of from about 21 psia to about 66 psia. An azeotropic or azeotrope-like composition having about 80±5 weight percent HF and about 20±5 weight percent HCFC-224aa has been found to boil at about 28° C. and 21 psia. An azeotropic or azeotrope-like composition of about 75±5 weight percent HF and about 25±5 weight percent HCFC-224aa has been found to boil at about 44° C. and 35 psia.

In another preferred embodiment of the invention, of HCFC-224aa may be removed from a mixture containing of HCFC-224aa and an impurity which may, for example, result from manufacturing steps in the preparation of HCFC-224aa. This is done by adding hydrogen fluoride to a mixture of HCFC-224aa and the impurity. Hydrogen fluoride is added to the mixture in an amount sufficient to form an azeotropic composition of HCFC-224aa and hydrogen fluoride, and thereafter the azeotropic composition is separated from the impurity, for example by distillation, scrubbing, or other art recognized separating means. Preferably, the impurity itself does not form a close-boiling azeotropic mixture with HCFC-224aa, hydrogen fluoride or a mixture of HCFC-224aa and hydrogen fluoride. As used herein, the term close-boiling azeotropic mixture means an azeotropic mixture having a boiling point within 10° C. of the azeotropic mixture of the invention.

The following non-limiting examples serve to illustrate the invention.

EXAMPLE 1

20 g of 1,2,2-trichloro-1,3,3,3-tetrafluoropropane (HCFC-224aa) is dissolved in 80 g of HF to form a heterogeneous mixture. The vapor pressure of the mixture at 28° C. is 21 psia.

EXAMPLE 2

25 g of 1,2,2-trichloro-1,3,3,3-tetrafluoropropane is dissolved in 75 g of HF to form a heterogeneous mixture. The vapor pressure of the mixture at 44° C. is 35 psia.

EXAMPLE 3

Binary compositions consisting essentially of 1,2,2-trichloro-1,3,3,3-tetrafluoropropane (HCFC-224aa) and HF were blended to form heterogeneous mixtures. Vapor-Liquid-Liquid equilibrium was carried out at the temperature range of 28 to 65° C. The compositions of the upper liquid phase, the bottom phase and the vapor phase were sampled. The vapor pressure of the mixture was also recorded. The results are shown in Table 1. Note that the vapor pressure of HF at 28.3° C. is 19.8 psia and that of HFC-224aa is about 1 psia. From this table it is observed that the vapor pressure of the mixture is higher than the vapor pressure of each individual components. From this example it is determined that the azeotropic composition is about 80 weight percent HF at 28° C. and about 75 weight percent HF at 44° C.

TABLE 1

| | | Composition (Wt. % HF) | | |
|---|---|---|---|---|
| Temperature (° C.) | Pressure (Psia) | Bottom Liquid Phase | Upper Liquid Phase | Vapor Phase |
| 28.3 | 21.3 | 0.48 | 93.4 | 79.7 |
| 43.6 | 34.6 | 0.64 | 92.5 | 75.6 |
| 65.1 | 65.7 | 0.92 | 75.6 | 15.3 |

What is claimed is:

1. An azeotropic composition consisting essentially of 1,2,2-trichloro-1,3,3,3-tetrafluoropropane and hydrogen fluoride.

2. An azeotropic or azeotrope-like composition consisting essentially of from about 1 to about 95 weight percent hydrogen fluoride and from about 5 to about 99 weight percent 1,2,2-trichloro-1,3,3,3-tetrafluoropropane, which composition has a boiling point of from about 28° C. to about 65° C. at a pressure of from about 21 psia to about 66 psia.

3. The composition of claim 2 which consists of hydrogen fluoride and 1,2,2-trichloro-1,3,3,3-tetrafluoropropane.

4. The composition of claim 2 wherein the hydrogen fluoride is present in an amount of from about 15 to about 80 weight percent.

5. The composition of claim 2 wherein the hydrogen fluoride is present in an amount of from about 70 to about 80 weight percent.

6. The composition of claim 2 having a boiling point of about 28° C. at a pressure of about 21 psia.

7. The composition of claim 2 having a boiling point of about 44° C. at a pressure of about 35 psia.

\* \* \* \* \*